(12) United States Patent
Renn et al.

(10) Patent No.: US 6,656,974 B1
(45) Date of Patent: Dec. 2, 2003

(54) FOAM MATERIALS

(75) Inventors: Donald W. Renn, Glen Cove, ME (US); Yimin Qin, Northwich (GB); Chiara Rossetto, Warrington (GB)

(73) Assignee: Advanced Medical Solutions Limited (GB)

( * ) Notice: Subject to any disclaimer, the term of this patent is extended or adjusted under 35 U.S.C. 154(b) by 0 days.

(21) Appl. No.: 09/529,563

(22) PCT Filed: Oct. 19, 1998

(86) PCT No.: PCT/GB98/03106

§ 371 (c)(1), (2), (4) Date: Sep. 21, 2000

(87) PCT Pub. No.: WO99/20318

PCT Pub. Date: Apr. 29, 1999

(30) Foreign Application Priority Data

Oct. 17, 1997 (GB) ............................................. 9721930
Oct. 24, 1997 (GB) ............................................. 9722371

(51) Int. Cl.[7] ...................... A61K 31/738; A61K 47/36; B01F 3/04; B01F 17/48

(52) U.S. Cl. ................ 516/11; 424/78.06; 428/311.51; 514/779; 514/945; 516/18; 516/19; 516/105; 516/106

(58) Field of Search .............................. 516/10, 11, 18, 516/19, 105, 106; 424/78.06; 514/945, 779

(56) References Cited

U.S. PATENT DOCUMENTS

| | | | | |
|---|---|---|---|---|
| 2,764,512 A | * | 9/1956 | Wilson | 516/105 X |
| 3,119,698 A | * | 1/1964 | Gunther | |
| 3,334,052 A | * | 8/1967 | Kurz et al. | 516/105 |
| 4,793,337 A | * | 12/1988 | Freeman et al. | 604/368 X |
| 5,352,709 A | * | 10/1994 | Tarrant et al. | 521/84.4 |
| 5,470,576 A | * | 11/1995 | Patel | 424/445 |
| 6,187,290 B1 | * | 2/2001 | Gilchrist et al. | 424/78.07 X |
| 6,270,794 B1 | * | 8/2001 | Cilento et al. | 424/78.06 X |

FOREIGN PATENT DOCUMENTS

| | | | |
|---|---|---|---|
| DE | 195 05 709 | * | 8/1996 |
| EP | 0 613 693 | * | 9/1994 |
| WO | WO 91/11205 | * | 8/1991 |
| WO | WO 96/13285 | * | 5/1996 |

* cited by examiner

*Primary Examiner*—Richard D. Lovering
(74) *Attorney, Agent, or Firm*—Woodard, Emhardt, Moriarty, McNett & Henry LLP

(57) ABSTRACT

An absorbent foam material which comprises a solid, cross-linked form of an anionic polymer (e.g. an alginate) and fibers or other cation contributing polymeric particulates which have donated appropriate cations for effecting cross-linking of the anionic polymer. Methods of producing the foam material are also disclosed.

15 Claims, No Drawings

FOAM MATERIALS

This application is a 371 of PCT/GB98/03106 filed Oct. 19, 1998.

The present invention relates to foam materials which are useful particularly but not exclusively as wound dressings.

It is well know that various materials having useful properties (e.g. for the production of wound dressings) may be produced by cross-linking of water soluble anionic polymeric materials (e.g. hydrocolloids).

Thus for example alginate fibres may be produced by spinning an alginate solution into a coagulating bath containing cations (e.g. $Ca^{2+}$) capable of cross-linking the alginate thus resulting in fibre production. Such fibres are highly absorbent and may be used in the form of a tow for packing a wound or may be formed into a mat, felt or the like as an alternative form of wound dressing. Furthermore, it is known to product alginates in the form of a dehydrated hydrogel by a process in which an alginate hydrogel is treated with fibres (e.g. calcium alginate fibres) which provide cations for cross-linking the alginate in the hydrogel followed by removal of water to produce a cross-linked, dehydrated hydrogel containing the fibres as reinforcement (see WO-A-96/13285). Such a hydrogel may also be used as a wound dressing.

In all cases, the alginate provide high absorbency for the wound dressing so that relatively large amounts of wound-exudate may be taken up. This is a valuable property of the alginate for wound management. Furthermore, depending on the actual alginate polymer used, the dressing may be such that, in the wound, it retains its integrity so as to be removable in one-piece, or such that (in the wound) it becomes wet-dispersible so that it can be removed by irrigation. Depending on the nature of the wound, one or other method of removing the alginate may be desirable. Alginates are therefore very versatile materials for use as wound dressings.

In both cases, the alginate absorbs exudate and is converted into a moist gel on the wound. The wound may thus be maintained in a moist environment which is ideal for wound healing to take place.

There are however a number of disadvantages associated with the use of alignates in fibrous form for use as wound dressings. In particular, the process for producing the fibres is relatively lengthy and expensive involving, as it does, producing the dope, extrusion, washing, cutting the tow obtained by extrusion and carding of the staple fibre. Additionally, the carding step may break some of the fibres and those shorter fibres may be left as a residue in the wound. Furthermore, if the dope includes an agent to be incorporated in the fibre for delivery to the wound there is the danger that the agent will be "washed-out" of the fibre during the production process.

Similar disadvantages exist with cross-linked products produced from the types of water soluble anionic polymers (e.g. low-methoxyl pectin).

It is an object of the present invention to obviate or mitigate the abovementioned disadvantage.

According to a first aspect of the present invention there is provided an absorbent foam material which comprises a solid, cross-linked form of an anionic polymer and fibres or other polymeric particulates which have donated cations for effecting cross-linking of the anionic polymer.

Such "other polymeric particulates" may for instance comprise anionic polysaccharide particulates containing appropriate cross-linking ions.

As set out in the preceding paragraph, the anionic polymer is in a solid form which, in the context of the invention, describes the physical state of matter of the polymeric material rather than implying any particular physical property from the foam itself. Thus the foam may have various physical properties and may, for example, be a flexible or drapable material. Alternatively or additionally the foam may be compressible or resilient.

In view of the solid nature of the polymer, the foams may be regarded as self-supporting although we do not preclude the possibility of the foam incorporating or being associated with an additional supporting element as described more fully below.

According to a second aspect of the present invention there is provided a method of producing a foam material comprising generating a precursor foam comprising a solution of an anionic polymer in a solvent therefor and fibres or other polymeric particulates capable of donating cations for effecting cross-linking of said polymer, and converting the dissolved anionic polymer into a solid, form cross-linked by cations from said fibres or other particulates.

Foam materials in accordance with the invention may be produced (e.g. using the procedures described below) as highly conformable, absorbent material e.g. having a thickness of 1 to 5 mm and are eminently suitable for a variety of wound dressing applications, e.g. pressure sores, leg ulcers and other wounds with moderate to heavy exudate. For use as a dressing, the foam material may be used alone or may be juxtaposed (e.g. laminated) to at least one other type of wound dressing material. For example, the foam material may be used in conjunction with an alginate felt and/or a film of the type having a higher Moisture Vapour Transmission Rate (MVTR) capability in the presence of liquid water as compared to moisture vapour alone.

The anionic polymer which is cross-linked to produce the foam of the invention is preferably a water soluble polymer and may for example be a hydrocolloid. It is particularly preferred that the anionic polymer is a polysaccharide.

Examples of anionic polymers which may be used for the invention include alginates, low-methoxyl pectins, carrageenans, chrondoitin sulphate, hyaluronic acid, carboxymethyl cellulose, carboxymethyl starch, carboxymethyl guar, cellulose sulphate, dextran sulphate, gellan, xanthan, polyacrylic acid, a nucleic acid, or anionic derivatives of other hydrocolloids.

It is particularly preferred that the anionic polymer is an alginate.

Any number of a wide range of alginate polymers may be used in the invention. Thus, for example, the alginate may (prior to cross-linking) have a molecular weight of 200,000 to 1,000000 although it is generally preferred to use alginates towards the upper end of this range. More particularly, it is preferred to use an alginate having a viscosity of 600–800 cP for a 1% solution. Furthermore, the alginate used may have a wide range of G (Guluronic acid) and M (Mannuronic acid) values. Thus, for example, alginates which may be used in the present invention may have a G content of 30–70% and a M content of 70–30%. It is particularly preferred that the alginate has a G content of about 40% and an M content of about 60%.

A suitable alginate for use in the invention in Sobalg FD 156 (available from Danisco Ingredients).

In the production of foams of the invention, the anionic polymer is cross-linked by cations (preferably multivalent cations e.g. calcium) donated by fibres or other particulates with which the anionic polymer is admixed during production of the foam. The fibres/particulates may for example be of an insolubilised polysaccharide. Such fibres may be produced by spinning a solution of the polysaccharide into a bath containing cations which result in cross-linking of the polysaccharides to produce an insoluble fibrous form thereof capable of donating cations for effecting cross-linking of the anionic polymer. Alternatively the films may be formed by coagulating the polysaccharide in alcohol or a water miscible solvent. The fibrous structure generated by this latter technique may only be discernible under a microscope and as such are not fibres in the textile sense but nevertheless fall within the term "fibres" as used herein.

The fibres remain in the final foam to act as reinforcement. The fibres may for example be used in the form of a non-woven structure.

Examples of suitable fibres/particulates are calcium/sodium forms for which the calcium ions effect cross-linking. It is particularly preferred to use, as such fibres or particulates, those in which 60–85%, more preferably about 70%, of the alginic acid is in the form of the calcium salt with the remainder being in the form of the sodium salt. Preferably the fibres used have a G-content of about 40% and an M content of about 60%. Suitable fibres of this type are available under the designation MF1-21B from. Innovative Technologies.

It is particularly preferred to use fibres/particulates of this type since they swell in water and are easily dispersed meaning that the fibres can be used in a relatively long form, e.g. 10 to 50 mm. This gives rise to a smooth foam of good structure.

It is possible to use fibres or other polymeric particulates (such as polysaccharide particulates) in which substantially all of the cations are present as calcium ions. Such fibres are however less preferred since they are not so easy to disperse the need to be chopped to shorter length e.g. 5 to 10 mm than the calcium/sodium alginate fibres/particulates discussed above.

Foam materials in accordance with the invention may contain additional components to modify the properties thereof. Thus, for example, the foam may incorporate a hydrophilic polymer (e.g. carboxymethyl cellulose) to improve absorbency;

a bulking/bodying agent such as a water absorbing or adsorbing insoluble solid, e.g. cellulose, microcrystalline cellulose, clays or other insoluble hydrocolloids (as fibres or particulates);

a humectant/plasticiser such as glycerol, propylene glycol, polyethylene glycol, PEO/PPO polymer, mannitol, sorbitol;

a wound healing agent, for example Ace Mannan (or other components of Aloe vera) for its wound healing capability, epidermal and/or other growth factors, zinc, silver or enzymes; and soluble hydrocolloids to impart a desired function, e.g. locust bean gum or guar gum for freeze-thaw protection.

The foam material of the invention may be used as a drug delivery system by incorporation of a drug in the foam.

The foam material of the invention may also incorporate activated charcoal (e.g. in powdered or granular form) for the purposes of adsorbing odours.

Foams in accordance with the invention are produced by generating a precursor foam from a solution (e.g. in water) of the anionic polymer, which precursor foam also contains the fibres/particulates for donating the cations to cross-link the anionic polymer. The precursor foam may be in the form of a gel which is then cast prior to removal of solvent to provide the solid form of the cross-linked polymer.

The foam may be generated, for example, by physical whipping, pressure differential (high to low), chemical reaction (e.g. acids plus carbonates/bicarbonates), air or other gas sparging, or extrusion.

For the purpose of generating the foam, the solution of the anionic polymer preferably includes a foam generating or foam stabilising agent. It is particularly preferred that a foam-stabilising hydrocolloid is used.

It is particularly preferred that the foam stabilising agent is hydroxypropyl cellulose (particularly a pharmaceutical grade thereof). The hydroxypropyl cellulose may, for example, by Klucel 99-GF EP. It is however possible also to use other polysaccharide (e.g. cellulose) derivatives, e.g. hydroxyethyl cellulose, methyl ethyl cellulose, methyl cellulose and hydroxypropyl starch. Non-cellulosic materials are less preferred as foam generating agents but can be used in accordance with the invention. Examples of non-cellulosic foam generating agents which may be used are ionic or non-ionic surfactants such as those available under the name TWEEN, e.g. TWEEN 20 (BP GRADE).

To produce a foam in accordance with the invention, it is generally preferred that the soluble anionic polymer, the foam generating/stabilising agent, and the fibres or other cation contributing particulates are made up of separate solutions/dispersions which may then be mixed together.

Typically, the solutions/dispersions of the anionic polymer, fibres and foam generating/stabilising agent will each comprise 0.1% to 5%, more usually 0.5% to 2% by weight of the respective components. It should however be appreciated that the nature of the anionic polymer used and/or its concentration in the solution will influence the porosity and flexibility of the ultimately obtained foam. The skilled person will be readily able to achieve the required properties for a particular foam by varying the amount of alginate polymer.

Any of these solutions/dispersions to be admixed together may incorporate desired additional components (e.g. glycerol) to be included in the foam.

Once the three solutions have been added together, mixing may be effected so as to produce a solution of the maximum volume which can be obtained without any breaking down the gel structure.

The mixture thus obtained may then be cast onto a suitable substrate and then dried. Typically the mixture is cast to a thickness of 10 to 20 mm and dried to a thickness of 1 to 3 mm. The substrate may be one from which the foam is removed prior to its ultimate use or other which is maintained in contact with the foam for such use. The substrate onto which the mixture is cast may, for example, be a film (such as a polyurethane film), a felt (e.g. alginate felt), a gauze or a cloth. It is also possible to cast the foam such as to incorporate a support material internally of the foam. Drying may for example be effected in an oven although it is possible to use freeze-drying, water-miscible solvent drying, quiescent drying, forced air drying or vacuum drying.

The product of the above procedure is a highly absorbent and conformable foam which is eminently suitable for use as a wound dressing.

If desired, the foam can be given a coating of any number of materials, including solid particulates (including powders) before drying or can be coated or dipped in other solutions after drying, and then redried to impart useful desired properties, to leach any soluble components, or chemically to treat one or more components such as by ion-exchanging.

If desired the foam may be sterilised by the use of γ-radiation although this may result in a reduction in absorbency and integrity of the foam.

Furthermore, if desired, the foam may be comminuted to produce particles.

The abovedescribed method of producing a wound dressing (i.e. the foam) has a number of advantages as compared to the production of fibrous dressings. In particular, the process is simple to carry out and components for incorporation in the foam may readily be incorporated in one or more of the solutions from which the foam is produced are thereby incorporated in the foam without subsequently being lost therefrom.

As indicated, the foam materials are eminently suitable for use as wound dressings. In particular, the foams are highly absorbent so as to be capable of providing a moist environment for wound healing. It will of course be appreciated that the disadvantages of broken fibres encountered in the case of fibrous dressings does not apply to foams.

The foam material may be used in conjunction with a breathable film which is increased MVTR capability in the presence of liquid water as compared to moisture vapour only. MVTR in the presence of liquid water may be measured by ASTM E96BW whereas MVTR in the presence of moisture vapour alone may be measured by ASTM E96B (water method). Preferably the value of the breathability in the presence of liquid water is at least twice and preferably at least three times that in the presence of moisture vapour alone. The value may be up to 30 to 409 times that for moisture vapour alone. Typically the film will be of a material which has an MVTR in the presence of moisture vapour since (ASTM E96BW) in the range 6,000 to 30,000 g m$^{-2}$ 24 hr$^{-1}$ (e.g. 600 to 10,000 g m$^{-2}$ 24 hr$^{-1}$). Typically the film will have a thickness of 30–70 microns more preferably 40–60 microns, e.g. about 50 microns.

The film may for example be of polyurethane. Suitable films are available from Innovative Technologies Limited under the designations B532, C542 and D562.

It is not however essential that the foam material be used as a wound dressing. Other applications include use as absorbent pads for diapers and other products, face and skin cleansers and controlled release delivery systems.

The invention will be further described by reference to the following non-limiting examples.

EXAMPLE 1

A dispersion and two solutions of the following compositions were produced in accordance with the procedures described below.

Dispersion 1:

3 g MF1-21B Fibres (Sodium/Calcium Alginate Fibres) cut to 50 mm length 200 ml Distilled Water Solution 1:

5 g Sobalg FD 156 (sodium alginate powder, ex Danisco Ingredients, Suffolk, England)

5 g Glycerol 300 ml Distilled Water

Solution 2:

1.5 g Klucel 99 GF EP (hydroxypropyl cellulose, ex Hercules Limited)

4 g Glycerol 200 ml Distilled Water 0.4 g Tween 20 BP grade

Dispersion 1 was prepared by dispersing the MF1-21B fibres in the distilled water using a paddle mixture. Each of solutions 1 and 2 were produced using a high speed mixer. Solution 2 thus prepared incorporated a multitude of air bubbles.

Solution 2 was then poured into Dispersion 1 followed by solution 1 and mixing effected using a Hobart Food Mixer for about 20 minutes resulting in a thick, foaming mixture. This mixture was then spread into a 30 cm×40 cm rectangle on a perforated sheet covered by a cloth. The perforated sheet was then placed in an oven at 90° C. for about 1 hour and then dried at 50° C. for 15 hours.

After removal from the oven, the foam was allowed to cool to room temperature and then peeled from the cloth. A portion of the foam was sterilised using γ-radiation and various tests were then conducted on the sterilised and unsterilised products.

The foam had good conformability and, as can be seen from Table 1, had high absorbency and was "wet dispersible" in the "Wet Integrity" test. The foam is eminently suitable for use as a wound dressing.

It will be seen from Table 1 that both the sterilised and non-sterilised forms of the foam had high absorbency and good wet strength whilst remaining "integral" in the "Wet Integrity" test. The foam is eminently available for use as a wound dressing in view of these properties together with the potential wound healing capability and the haemeostatic properties.

TABLE 1

|  |  | EXAMPLE 1 |
| --- | --- | --- |
| Weight | sterile | 229.4 |
| g/m$^2$ | unsterile | 236.84 |
| Absorbency | sterile | 5.33; 15.55 |
| g/g; g/100 cm$^2$ | unsterile | 20.2; 47.42 |
| Wet Integrity | sterile | Dispersible |
|  | unsterile | Integral |
| wet strength | sterile | n/a |
| N; % | unsterile | n/a |
| pH (25° C.) | sterile | 6.1 |
|  | unsterile | 6.3 |

EXAMPLE 2

A dispersion and two solutions of the following compositions were produced using the techniques described in Example 1.

Dispersion 1:

7.2 g MFI-21B fibres (Sodium/Calcium fibres) cut to 50 mm length 300 ml Distilled Water Solution 1:

12 g Solbag FD 155 (Sodium Alginate Powder)

600 g Distilled Water

Solution 2:

4.8 g Klucel 99-GF EP (hydroxypropyl cellulose)

24 g Glycerol 400 ml Distilled Water

The procedure described in Example 1 was used to produce a foam from this dispersion and these two solutions save that sterilisation was effected with ethylene oxide (1.7 bar) (rather than γ-radiation) to preserve wet strength.

Table 2 below shows the properties of the resulting foam.

TABLE 2

| Weight/unit area | 228.2 g/100 cm$^2$ |
| --- | --- |
| Absorbency | 63.6 ± 3.8 g/100 cm$^2$ |
|  | 20.7 ± 2.9 g/g |
| Wet integrity | Integral |

What is claimed is:

1. A method of producing an absorbent foam material suitable for use as a wound dressing, the method comprising generating a precursor foam comprised of a solution of an anionic alginate polymer in a solvent therefor and being further comprised of calcium/sodium alginate fibres or other calcium/sodium alginate particulate material, said fibres or other particulate material being capable of donating calcium cations for effecting cross-linking of the anionic alginate polymer, and effecting cross-linking of the anionic alginate polymer by said calcium cations from the fibres or other particulate material so as to convert the anionic alginate polymer into a solid form thereby providing said absorbent foam material wherein the fibres or other particulate material comprise 60 to 85% of the alginic acid in the form of the calcium salt with the remainder being in the form of the sodium salt.

2. A method as claimed in claim 1 further comprises an anionic polymer selected from the group consisting of: low-methoxyl pectins, carrageenans, chrondoitin sulphate, hyaluronic acid, carboxymethyl cellulose, carboxymethyl starch, carboxymethyl guar, cellulose sulphate, dextran sulphate, gellan, xanthan, polyacrylic acid, a nucleic acid, and anionic derivatives of other hydrocolloids.

3. A method as claimed in claim 1 comprising preparing a solution of the anionic alginate polymer containing said calcium/sodium alginate fibres or other calcium/sodium alginate particulate material and effecting foaming of said solution to produce said precursor foam.

4. A method as claimed in claim 1 wherein the anionic alginate polymer has a molecular weight of 200,000 to 1,000,000.

5. A method as claimed in claim 4 wherein the anionic alginate polymer is one having a viscosity of 600–800 cP for a 1% solution thereof.

6. A method as claimed in claim 4 wherein the anionic alginate polymer has a G-content of 30–70% by mole and a M-content of 70–30% by mole.

7. A method as claimed in claim 6 wherein the anionic alginate polymer has a G-content of about 40% by mole and a M-content of about 60% by mole.

8. A method as claimed in claim 1 wherein the calcium/sodium alginate fibres or other calcium/sodium alginate particulate material have a G-content of about 40% and M-content of about 60%.

9. A method as claimed in claim 1 wherein said precursor foam is generated with the aid of a foaming agent.

10. A method as claimed in claim 9 wherein the foaming agent is a cellulose derivative.

11. A method as claimed in claim 10 wherein the foaming agent is hydroxypropyl cellulose.

12. A method as claimed in claim 1 wherein the foam produced has a thickness of 1 to 5 mm.

13. A method as claimed in claim 1 wherein the foam produced incorporates at least one of a hydrophilic polymer to improve absorbency, a bulking/bodying agent, a humectant/plasticiser, a wound healing agent or other therapeutic or physiologically active substance, a soluble hydrocolloid, a salt and a sugar.

14. A method as claimed in claim 13 wherein the foam produced incorporates glycerol as a plasticiser.

15. A method as claimed in claim 1 wherein the foam produced incorporates activated charcoal.

* * * * *